United States Patent [19]

Ruff et al.

[11] Patent Number: 5,358,970
[45] Date of Patent: Oct. 25, 1994

[54] PHARMACEUTICAL COMPOSITION CONTAINING BUPROPION HYDROCHLORIDE AND A STABILIZER

[75] Inventors: Michael D. Ruff, Greenville, N.C.; Sanyasi R. Kalidindi, Edison, N.J.; Joel E. Sutton, Jr., Greenville, N.C.

[73] Assignee: Burroughs Wellcome Co., Research Triangle Park, N.C.

[21] Appl. No.: 105,437

[22] Filed: Aug. 12, 1993

[51] Int. Cl.$^5$ ............................................. A61K 31/135
[52] U.S. Cl. .................................... 514/649; 514/769; 514/772
[58] Field of Search ......................................... 514/649

[56] References Cited

U.S. PATENT DOCUMENTS

| | | |
|---|---|---|
| 33,994 | 7/1992 | Baker et al. |
| 3,819,706 | 6/1974 | Mehta |
| 3,885,046 | 5/1975 | Mehta |
| 4,347,176 | 8/1982 | Mehta |
| 4,347,177 | 8/1982 | Phillips |
| 4,347,178 | 8/1982 | Findlay et al. |
| 4,347,257 | 8/1982 | Stern |
| 4,347,382 | 8/1982 | Scharver |
| 4,355,179 | 10/1982 | Findlay et al. |
| 4,356,165 | 10/1982 | Findlay |
| 4,393,078 | 7/1983 | Peck |
| 4,425,363 | 1/1984 | Stern |
| 4,435,449 | 3/1984 | Stern |
| 4,438,138 | 3/1984 | Stern |
| 4,507,323 | 3/1985 | Stern |
| 4,571,395 | 2/1986 | Peck |
| 4,687,660 | 8/1987 | Baker et al. |
| 4,769,027 | 9/1988 | Baker et al. |
| 4,798,826 | 1/1989 | Peck |

FOREIGN PATENT DOCUMENTS 2134516 8/1984 United Kingdom .

OTHER PUBLICATIONS

Laizure et al. Ther. Drug Monit. 7(y):447–458 1985 "Stability of Bupropion" GA. 10y: 814822 (1985).

Billinghurst et al GA.101:210748e (1985) of U.K. 2134516(Aug. 15, 1984) (Maleate Salt More Stable Than Other Salt Forms Prep,d,e.g. citrate, furmate).

Steven M. Walters; Influence of pH on Hydrolytic Decomposition of Diethylopropion Hydrochloride: Stability Studies on Drug Substance and Tablets Using High–Performance Liquid Chromatography; Journ. of Pharm. Sciences; vol. 69; No. 10; Oct. 1980; pp. 1206–1209.

*Primary Examiner*—Shep Rose
*Attorney, Agent, or Firm*—Donald Brown; Lawrence A. Nielsen; Wayne R. Eberhardt

[57] ABSTRACT

This application discloses a method of inhibiting degradation of the antidepressant bupropion hydrochloride in a solid pharmaceutical formulation, so that the pharmaceutical formulation will maintain at least 80% of its initial bupropion potency after one year.

17 Claims, No Drawings

PHARMACEUTICAL COMPOSITION CONTAINING BUPROPION HYDROCHLORIDE AND A STABILIZER

BRIEF BACKGROUND OF THE INVENTION

Bupropion hydrochloride is a well known antidepressant sold in instant release tablet form under the brand name WELLBUTRIN ® by Burroughs Wellcome Co. in the United States. Also see U.S. Pat. Nos. 3,819,706 and 3,885,046 and 1993 Physicians Desk Reference.

While the instant release tablets currently sold are quite suitable and degradation of bupropion hydrochloride is successfully prevented, the method of manufacturing same is less then desirable based on cost as well as process conditions.

The present invention describes a method to prevent (inhibit) the degradation of bupropion hydrochloride, using stabilizer ingredients, thus allowing the preparation of instant and sustained release tablets and capsules which from a cost of manufacture and processing condition standpoint are much improved over that achievable in the past.

DESCRIPTION OF THE INVENTION

This invention is particularly directed to a new and improved method for stabilizing the antidepressant bupropion hydrochloride, i.e. preventing (inhibiting) its decomposition so that it may be used in a pharmaceutical preparation, e.g. a tablet, and still retain at least 80% of its potency and preferably at least 90% after one year of storage at room temperature (59°–77° F.) at 35–60% humidity. For example if the tablet initially contains 100mg bupropion hydrochloride (labeled amount) at time of preparation, after one year storage at least 80mg of bupropion hydrochloride will remain in the tablet.

Bupropion hydrochloride (HCl) is disclosed in the aforementioned patents as well as in the Merck Index, Eleventh Edition, entry No. 1488.

Accordingly this invention also includes as a feature of the invention a tablet or capsule containing an effective stabilizing amount of a stabilizer according to this invention.

As used herein, the term stabilizer means a composition which inhibits (prevents) the decomposition of bupropion hydrochloride.

The stabilizers which are suitable for use in this invention are those which have an aqueous solution pH of about 0.9 to about 4 at an aqueous solution concentration of about 6% w/w and are a solid or liquid at 30° C.

The aqueous solution pH of the stabilizers of this invention is determined as follows:

The stabilizer is weighed out to provide 3.750 grams thereof, (except for 3.344 grams of L-cystine dihydrochloride) and is then added to 60 grams of distilled water in a glass Pyrex ® beaker. The resulting mixture is stirred for approximately 5 minutes, using a stir plate and magnetic stir bar. The resulting solution or dispersion is examined using either a Orion Model 701A Ionalyzer ®, or an Accumet pH Meter Model 915. Solutions are stirred with a magnetic stir bar during analysis. Measurements of pH are performed in triplicate and the average thereof is used.

The stabilizers which meet the aforementioned pH range and are therefore useful in this invention include: L-cysteine hydrochloride, glycine hydrochloride, ascorbic acid, malic acid, sodium metabisulfite, isoascorbic acid, citric acid, tartaric acid, L-cystine dihydrochloride. L-cysteine hydrochloride and glycine hydrochloride are the most preferred stabilizers.

The amount of the stabilizer which should be used to achieve the results desired, for stabilization of bupropion hydrochloride in pharmaceutical solid dosage formulations, e.g. tablets and capsules, is about 2.7% to 27%, most preferably about 5% to 16.2% based on the label strength of bupropion hydrochloride in the pharmaceutical formulation (composition) in solid form.

In the examples the cystsine hydrochloride is in the L form and NF and USP are designations for standards published in the National Formulary and U.S. Pharmacopeia, respectively.

It should be understood that combinations of stabilizers may be used which meet the aforementioned pH conditions.

The pharmaceutical compositions prepared in accordance with this invention are solid in form and when stored for 6 weeks at about 50° C. and about 27% relative humidity contain at least about 80% of the amount of the bupropion hydrochloride in the composition at the time of storage under these conditions. The composition of this invention preferably is one wherein the weight of bupropion hydrochloride in the tablet is Y and the amount of inactive ingredients is greater than about 50% of Y and less than about 400% of Y. The tablet or capsules in this invention generally contain 25 mg to 500 mg of bupropion hydrochloride and usually contain 50 mg, 75 mg, 100 mg or 150 mg of bupropion hydrochloride.

Thus the present invention provides both a method of stabilizing bupropion hydrochloride to slow the degradation thereof by admixing the stabilizer with bupropion hydrochloride as well as solid form pharmaceutical formulations in which the bupropion hydrochloride is inhibited from degrading at a rate which would prevent it from being a product that can be stored over a prolonged period of time at room temperature i.e. under humidity and temperature conditions usually encountered in pharmacies and in medicine cabinets. With the solid form compositions of this invention the amount of bupropion hydrochloride will be prevented from being reduced to less than 80% of its labeled strength, and more preferably not less than 90% percent of the labeled strength after one year of storage under the aforementioned usually encountered conditions.

To determine the amount of active ingredient in the tablet after storage, standard procedures such as high performance liquid chromatography (HPLC) may be used.

As used herein caplets are tablets generally shaped in the form of capsules.

Capsules of this invention are generally prepared by mixing the stabilizer with bupropion hydrochloride and other excipients and placing same in, e.g., a two-part hard gelatin capsule.

The following examples are representative of the invention.

In the examples, cystsine hydrochloride means L-cysteine hydrochloride.

EXAMPLE 1

The formulation contained the following ingredients in the following amounts:

| Ingredient | Weight (mg) per tablet | |
|---|---|---|
| | 100 mg potency | 75 mg potency |
| Bupropion hydrochloride | 100.0 | 75.0 |
| Microcrystalline cellulose, NF | 91.3 | 68.5 |
| Sodium starch glycolate, NF | 9.2 | 6.9 |
| L-Cysteine hydrochloride, NF | 5.0 | 3.8 |
| Talc, USP | 23.0 | 17.3 |
| Magnesium stearate, NF | 1.2 | 0.9 |
| Colloidal silicon dioxide, NF | 0.3 | 0.2 |
| TOTAL | 20.0 mg | 172.6 mg |

The powder ingredients were weighed out for a 120,000 tablet batch size for the 100 mg potency and a 160,000 tablet batch size for the 75 mg potency.

The bupropion hydrochloride, microcrystalline cellulose and sodium starch glycolate were sifted through 30 mesh a Russell-Finex sifter.

The sifted ingredients were blended for 15 minutes in a 3 cu. ft. slant-cone blender.

The blended ingredients were granulated as follows:

The cystsine hydrochloride was dissolved in 1.28kg of purified water using a Lightnin' ® Mixer. This cystsine hydrochloride solution was added to 5.12 kg of SD3A alcohol (anhydrous) and mixed thoroughly using a Lightnin' ® Mixer. The blended ingredients were placed in a 3 cu. ft. Littleford Lodige granulator and granulated using the cystsine hydrochloride solution. Mixing time was 3 to 5 minutes and chopper time was 3 to 5 minutes. Wetness was checked and additional 80% w/w SD3A alcohol (aqueous) solution was added to achieve appropriate massing.

Clumps of wet granule were broken up by hand.

Granule was dried in a WST-30 Glatt fluid-bed dryer until loss on drying (by Compu-Trac ®, 90° C.) of granule was between 1 to 2%. Fluid-bed dryer parameters were set as follows:

Inlet air temperature: 60° C.
Air volume: 200–800 cu. meter/hr.
Pro-heat temperature: 25° C.
Dew point: 10° C.
By-pass flap: 50%
Shaker interval: 5 seconds every 2 minutes Dried granule was sifted through a 20 mesh Russell-Finex sifter.

Talc (pro-sifted 60 mesh) was added to a small amount of dried granule, sifted through a 20 mesh Russell Finex sifter, added to a 3 cu. ft. slant-cone blender and blended with the remainder of the granule for 5 minutes. Magnesium stearate and colloidal silicon dioxide was sifted together through a 30 mesh Russell-Finex sifter and blended in a table-top v-shell blender for 20 minutes. This magnesium stearate/colloidal silicon dioxide blend was then added to the dried granule in the 3 cu. ft. slant-cone blender and blended an additional 5 minutes.

The lubricated granule was compressed on a rotary-type Manesty Betapress ® in a controlled humidity environment of less than 30% relative humidity. Tablets were compressed at a compression weight of about 230 mg for the 100 mg potency and about 172.6 mg for the 75 mg potency. Round, 7.8 mm, concave, plain punches were used for the 100mg potency and round, 7.0 mm concave, plain punches were used for the 75 mg potency.

Tablets were dedusted using a Manesty Tablet Deduster.

A portion of tablets was film-coated using a COMPU-LAB Acella-Cota ® film-coater. The aqueous film coat Opadry ® Red YS-1-1846 was used for the 100 mg potency and Opadry ® Yellow YS-1-2186 for the 75 mg potency (supplied by Colocon, Inc. of 415 Moyer Blvd., West Point, Penna. 19486). The Accela-Cora ® parameters were:

Inlet air temperature:50°–80° C.
Inlet air volume:100–500 cfm
Exhaust air temperature:50°–60° C.

Tablets were coated to a weight gain of 1–5% based on the core tablet weight to achieve an acceptable color intensity.

EXAMPLE 2

The procedure of Example 1 was repeated except that lubricant levels were changed, resulting in the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| L-Cysteine hydrochloride | 5.0 |
| Talc, USP | 23.0 |
| Magnesium stearate, NF | 2.4 |
| Colloidal silicon dioxide, NF | 0.6 |
| TOTAL | 231.5 |

EXAMPLE 3

The procedure of Example 2 was repeated except;

In order to achieve a 75 mg potency, the tablets were compressed using 7.0 mm, round, concave, plain punches and were not film-coated. Tablets had the resulting formulation:

| Ingredient | 75 mg potency tablet Weight (mg) per tablet |
|---|---|
| Bupropion hydrochloride | 75.0 |
| Microcrystalline cellulose, NF | 68.5 |
| Sodium starch glycolate, NF | 6.9 |
| L-Cysteine hydrochloride | 3.8 |
| Talc, USP | 17.3 |
| Magnesium stearate, NF | 1.8 |
| Colloidal silicon dioxide, NF | 0.5 |
| TOTAL | 173.8 |

EXAMPLE 4

Tablets are manufactured according to the following formulation:

| Ingredient | 100 mg potency tablet Weight (mg) per tablet |
|---|---|
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 23.0 |
| Magnesium stearate, NF | 1.2 |
| Colloidal silicon dioxide, NF | 0.32 |
| TOTAL | 230.0 mg |

Sufficient powder ingredients were weighed out to make approximately 24,000 tablets.

The bupropion hydrochloride, microcrystalline cellulose and sodium starch glycolate were sifted through a 30 mesh Russell-Finex sifter.

The sifted ingredients were blended for 15 minutes in a Patterson-Kelly (PK) v-shell blender. The blended ingredients were granulated as follows:

A quantity of purified water, USP that equals approximately 25% of the total weight of granulating solvent needed to impart the desired granule wetness was weighed out. The glycine hydrochloride was dissolved in the purified water using a Lightnin' ® Mixer. The glycine hydrochloride solution was added to a quantity of SD3A alcohol, anhydrous, equal to the remaining 75% of the total weight of solvent needed to impart the desired granule wetness and mixed thoroughly using a Lightnin' ® Mixer. The blended ingredients were placed in a Hobart planetary mixer and granulated using the glycine hydrochloride solution. Mixing and time was approximately 3 to 5 minutes. Granulation wetness was checked and additional 75% w/w SD3A alcohol (aqueous) solution was added to achieve appropriate massing.

Any clumps of wet granule were broken up by hand.

Granule was dried in a Despatch Tray Oven to 50° C. for approximately 4 hours until loss on drying (by Compu-Trac ®, 90° C.) of granule was 1 to 2%.

Dried granule was sifted through a 20 mesh Russell-Finex sifter.

Talc (pre-sifted 60 mesh) was added to a small amount of dried granule and sifted through a 20 mesh hand screen- This was added to the remainder of the granule and blended in a PK v-shell blender for 5 minutes- Magnesium stearate and colloidal silicon dioxide was sifted together through a 30 mesh hand screen, and blended in a PK v-shell blender for 15–20 minutes. This magnesium stearate/colloidal silicon dioxide blend was then added to the granule/talc blend in the PK v-shell blender and blended an additional 5 minutes.

The lubricated granule was compressed on a rotary-type Manesty Betapress ® in a controlled humidity environment of less than 30% relative humidity. Tablets were compressed at a compression weight of 230 mg, using 7.8 mm, round, concave, plain punches.

EXAMPLE 5

The procedure of Example 4 is repeated except that the lubricant levels are changed resulting in the following formulation:

| Ingredient | 100 mg potency tablet Weight (mg) per tablet |
| --- | --- |
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 22.9 |
| Magnesium stearate, NF | 0.7 |
| Colloidal silicon dioxide, NF | 0.2 |
| TOTAL | 229.3 mg |

Tablets are compressed at approximately 229.3 mg

EXAMPLE 6

The procedure of Example 4 is repeated except that the lubricant levels are changed resulting in the following formulation:

| Ingredient | 100 mg potency tablet Weight (mg) per tablet |
| --- | --- |
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 10.9 |
| Magnesium stearate, NF | 1.1 |
| Colloidal silicon dioxide, NF | 0.2 |
| TOTAL | 217.7 mg |

Tablets are compressed at approximately 217.7 mg

EXAMPLE 7

The procedure of Example 4 was repeated except that the lubricant levels were changed resulting in the following formulation:

| Ingredient | 100 mg potency tablet Weight (mg) per tablet |
| --- | --- |
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 10.9 |
| Magnesium searate, NF | 0.7 |
| Colloidal silicon dioxide, NF | 0.2 |
| TOTAL | 217.3 mg |

Tablets are compressed at approximately 217.3 mg

EXAMPLE 8

The procedure of Example 4 was repeated except magnesium stearate and colloidal silicon dioxide were replaced with sodium stearyl fumarate resulting in the following formulation:

| Ingredient | 100 mg potency tablet Weight (mg) per tablet |
| --- | --- |
| Bupropion hydrochloride | 100.0 |
| Microcrystalline cellulose, NF | 91.3 |
| Sodium starch glycolate, NF | 9.2 |
| Glycine hydrochloride | 5.0 |
| Talc, USP | 10.9 |
| Sodium stearyl fumarate | 3.3 |
| TOTAL | 219.7 mg |

Tablets are compressed at approximately 219.7 mg

EXAMPLE 9

The procedure of Example 4 was repeated except that the formulation is changed as follows:

| Ingredient | 100 mg potency tablet Weight (mg) per tablet |
| --- | --- |
| Bupropion hydrochloride | 100.0 |
| Microcrystalline cellulose, NF | 68.8 |
| Corn stach, NF | 2.0 |
| Sodium starch glycolate, NF | 9.2 |
| Glycine hydrochloride | 5.0 |
| Talc, USP | 23.0 |
| Magnesium stearate, NF | 0.8 |
| Colloidal silicon dioxide, NF | 0.2 |
| TOTAL | 230.0 mg |

Tablets are compressed at approximately 230.0 mg

EXAMPLE 10

The procedure of Example 4 is repeated except sodium starch glycolate is replaced with crospovidone, resulting in the following formulation:

| Ingredient | 100 mg potency tablet Weight (mg) per tablet |
|---|---|
| Bupropion hydrochloride | 100.0 |
| Microcrystalline cellulose, NF | 95.9 |
| Crospovidone | 4.6 |
| Glycine hydrochloride | 5.0 |
| Talc, USP | 2.0 |
| Magnesium stearate, NF | 1.2 |
| Colloidal silicon dioxide, NF | 0.3 |
| TOTAL | 230.0 mg |

Tablets are compressed at approximately 230.0 mg

EXAMPLE 11

The procedure of Example 4 is repeated except that the formulation is changed as follows:

| Ingredient | 100 mg potency tablet Weight (mg) per tablet |
|---|---|
| Bupropion hydrochloride | 100.0 |
| Microcrystalline cellulose, NF | 68.8 |
| Corn starch, NF | 23.0 |
| Sodium starch glycolate, NF | 9.2 |
| L-Cysteine hydrochloride | 5.0 |
| Talc, USP | 23.0 |
| Magnesium stearate, NF | 1.2 |
| Colloidal silicon dioxide, NF | 0.3 |
| TOTAL | 230.5 mg |

Tablets were compressed at approximately 230.5 mg

EXAMPLE 12

The procedure of Example 11 is repeated except that L-cysteine hydrochloride is replaced with glycine hydrochloride.

EXAMPLE 13

The procedure of Example 4 is repeated except that the sodium starch glycolate and colloidal silicon dioxide are removed and the formulation follows:

| Ingredient | 100 mg potency tablet Weight (mg) per tablet |
|---|---|
| Bupropion hydrochloride | 100.0 |
| Microcrystalline cellulose, NF | 71.0 |
| Corn starch, NF | 22.0 |
| L-Cysteine hydrochloride | 5.0 |
| Talc, USP | 22.0 |
| Magnesium stearate, NF | 1.1 |
| TOTAL | 221.1 mg |

Tablets were compressed at approximately 221.1 mg

EXAMPLE 14

The procedure of Example 4 was repeated except that the sodium starch glycolate was removed and the formulation follows:

| Ingredient | 100 mg potency tablet Weight (mg) per tablet |
|---|---|
| Bupropion hydrochloride | 100.0 |
| Microcrystalline cellulose, NF | 71.0 |
| Corn starch, NF | 22.0 |
| L-Cysteine hydrochloride | 5.0 |
| Talc, USP | 22.0 |
| Magnesium stearate, NF | 1.1 |
| Colloidal silicon dioxide, NF | 0.2 |
| TOTAL | 221.3 mg |

Tablets were compressed at approximately 221.3 mg.

A portion of tablets was film-coated using a Compu-Lab Accela-Cota ® film-coater. The aqueous film coat Opadry Red YS-1-1846 was used for the 100 mg potency. The Acelie-Cote ® parameters were:

Inlet air temperature: 50°–80° C.
Inlet air volume: 200–1000 cfm
Exhaust air temperature: 40°–60° C.
Exhaust air volume: 200–1000 cfm Tablets were coated to a weight gain of 1–5% over the core tablet weight to achieve an acceptable color intensity.

150 MG CAPSULES

EXAMPLE 15

150 mg capsules were prepared according to the following formulation and procedure:

| Ingredient | Weight (mg) per capsule |
|---|---|
| Bupropion hydrochloride | 150.0 |
| Microcrystalline cellulose, NF | 106.5 |
| Corn starch, NF | 33.00 |
| Talc, USP | 33.00 |
| L-Cysteine hydrochloride | 7.500 |
| TOTAL | 330.0 mg |

A stock blend of bupropion hydrochloride, corn starch and microcrystalline cellulose (MCC) was prepared as follows:

The above ingredients were sifted by hand through a 30 mesh screen. They were then blended in an Patterson-Kelly (P-K) v-shell blender for 10 minutes.

The proper amount of cysteine hydrochloride was weighed out and added to 85% w/w SD3A alcohol (aqueous) solution. This mixture was vigorously mixed for approximately 5 minutes. It was then immediately added to the proper amount of the above mentioned stock blend and wet-granulated in a table-top Hobart mixer.

The resulting wet granulation was screened by hand through a 16 mesh screen.

The wet granule was dried in a tray oven at 50° C. for 4 hours to obtain a loss on drying (LOD) of below 2% using a Compu-Trac ® moisture analyzer at 90° C. (Upon standing the batches re-equilibrated to 2–3% LOD).

The dried granule was sifted through a 16 or 30 mesh hand screen.

The granule was lubricated with talc (sifted 60 mesh), in a P-K v-shell blender for 5 minutes.

Finished granule is encapsulated on a Chemi-Pharm manual capsule-filling machine Model No. 201, using size No. 1, white, opaque two part hard gelatin capsules.

EXAMPLE 16

The procedure of Example 15 is repeated except cysteine hydrochloride was replaced with glycine hydrochloride.

EXAMPLE 17

The procedure of Example 15 is repeated except cysteine hydrochloride was replaced with L-cystine dihydrochloride.

EXAMPLE 18

The procedure of Example 15 is repeated except cysteine hydrochloride was replaced with tartaric acid.

EXAMPLE 19

The procedure of Example 15 is repeated except cysteine hydrochloride was replaced with citric acid.

EXAMPLE 20

The procedure of Example 15 is repeated except cysteine hydrochloride was replaced with malic acid.

EXAMPLE 21

The procedure of Example 15 is repeated except cysteine hydrochloride is replaced with isoascorbic (erythorbic) acid.

EXAMPLE 22

The procedure of Example 15 is repeated except cysteine hydrochloride is replaced with ascorbic acid.

EXAMPLE 23

The procedure of Example 15 is repeated except cysteine hydrochloride is replaced with sodium metabisulfite.

CAPLETS

EXAMPLE 24

The caplets were manufactured according to the following formulation:

| Ingredient | 100 mg potency caplet Weight (mg) per caplet |
|---|---|
| (Core) | |
| Bupropion hydrochloride | 100.0 |
| Microcrystalline cellulose, NF | 274.0 |
| Sodium starch glycolate, NF | 15.00 |
| L-Cysteine hydrochloride, USP | 9.000 |
| Talc, USP | 12.00 |
| Magnesium stearate, NF | 4.000 |
| CORE WEIGHT | 414.0 mg |
| (Coating) | |
| Opadry ® Red, YS-1-1846 | 12.00 |
| Carnauba Wax, NF | 0.0400 |
| TOTAL WEIGHT | 426.0 |

Sufficient powder ingredients were weighed out to make a batch size of approximately 60,000 caplets.

The bupropion hydrochloride, microcrystalline cellulose and sodium starch glycolate were sifted through a 20 or 30 mesh Russell Finex sifter.

The sifted ingredients were blended for 15 minutes in a 3 cu. ft. slant-cone blender.

The blended ingredients were granulated as follows:

A quantity of purified water, USP that equals approximately no more than 20% of the total weight of granulating solution needed to impart the desired granule wetness was weighed out. The cysteine hydrochloride was dissolved in the purified water using a mixer. The cysteine hydrochloride solution was added to a quantity of SD3A alcohol, anhydrous, equal to the remaining 80% (no less than) of the total weight of solution needed to impart the desired granule wetness and mixed thoroughly using a mixer. The blended ingredients were placed in a 3 cu. ft. Littleford Lodige ® granulator and granulated using the hydroalcoholic cysteine hydrochloride solution. Mixing and chopper time was approximately 5–10 minutes. Wetness was checked and additional 80% w/w SD3A alcohol (aqueous) solution was added to achieve appropriate massing.

Any clumps of wet granule were broken up by hand.

Granule was dried in a WST-30 Glatt fluid-bed dryer until loss on drying (by Compu-Trac ®, 90° C.) of granule was 0.8–2.0%. Fluid-bed drying parameters were set as follows:

Inlet air temperature: 60° C.
Air volume: 200–1200 cu. meter/hr.

Dried granule was milled using a Comil ® and appropriately sized screen.

Talc (pre-sifted 60 mesh) was added to a small amount of dried granule and mixed by hand. Magnesium stearate (pre-sifted) was added to a small amount of dried granule and mixed by hand. Both mixtures were sifted through a 16 mesh screen in a Russell Finex sifter. This sifted mixture was added to the remainder of the granule and blended in the. 3 cu. ft. slant-cone blender for 5 minutes.

The lubricated granule was compressed on a rotary-type Manesty Betapress ®. Caplets were compressed at a compression weight of approximately 414 gm, using 6.5×14.5 mm concave, caplet punches containing a partial score-bar on the upper and lower punches.

Caplets were dedusted using a Manesty Tablet Deduster

A portion of tablets was film-coated using a Compu-Lab Accela-Cota ® film-coater. The aqueous film coat Opadry Red ® YS-1-1846 was used. The Accela--Cota ® parameters were:

Inlet air temperature: 50°–80° C.
Inlet air volume: 100–500 cfm
Exhaust air temperature: 40°–60° C.

Caplets were coated to a weight gain of 1–5% over the core tablet weight to achieve an acceptable color intensity.

Caplets were coated with carnauba wax to assist in packaging. Carnauba wax was added to the film-coated caplets which were rotated in the coating drum for approximately 5 minutes to distribute the wax.

EXAMPLE 25

The procedure of Example 24 is repeated except:

In order to achieve a 75 mg potency, the caplets are compressed at a compression weight of approximately 310.5 mg, using 5.9×13.1 mm concave, caplet punches containing a partial score-bar on the upper and lower punches. The aqueous film coat Opadry ® Yellow-Gold YS-1-2186 was is for the 75 mg potency. Caplets have the resulting composition:

| Ingredient | 75 mg potency caplet Weight (mg) per caplet |
|---|---|
| (Core) | |
| Bupropion hydrochloride | 75.00 |
| Microcrystalline cellulose, NF | 205.5 |
| Sodium starch glycolate, NF | 11.25 |
| Cysteine hydrocloride, USP | 6.750 |
| Talc, USP | 9.000 |

-continued

| Ingredient | 75 mg potency caplet Weight (mg) per caplet |
|---|---|
| Magnesium stearate, NF | 3.000 |
| CORE WEIGHT | 310.5 mg |
| (Coating) | |
| Opadry Yellow, YS-1-2186 | 9.000 |
| Carnauba Wax, NF | 0.0300 |
| TOTAL WEIGHT | 319.5 mg |

EXAMPLE 26

The procedure of Example 24 is repeated except:
In order to achieve a 50 mg potency, the caplets are compressed at a compression weight of approximately 207 mg, using 5.1×11.4 mm concave, caplet punches containing a partial score-bar on the upper and lower punches. The aqueous film coat Opadry ® White YS-1-7059 is used for the 50 mg potency. Caplets have the resulting composition:

| Ingredient | 50 mg potency caplet Weight (mg) per caplet |
|---|---|
| (Core) | |
| Bupropion hydrochloride | 50.00 |
| Microcrystalline cellulose, NF | 137.0 |
| Sodium starch glycolate, NF | 7.500 |
| Cysteine hydrochloride, USP | 4.500 |
| Talc, USP | 6.000 |
| Magnesium stearate, NF | 2.000 |
| CORE WEIGHT | 207.0 mg |
| (Coating) | |
| Opadry White ®, YS-1-7059 | 6.000 |
| Carnauba Wax, NF | 0.0200 |
| TOTAL WEIGHT | 213.0 mg |

EXAMPLE 27

The procedure of Example 24 is repeated except:
The blended powders are granulated with 100% SD3A Alcohol.

EXAMPLE 28

The procedure of Example 27 is repeated except:
The cysteine hydrochloride is blended in dry with the other ingredients rather than adding it to the granulating solution.
The level of cysteine hydrochloride is increased giving the caplets the following composition:

| Ingredient | 100 mg potency caplet Weight (mg) per caplet |
|---|---|
| (Core) | |
| Bupropion hydrochloride | 100.00 |
| Microcrystalline cellulose, NF | 274.0 |
| Sodium starch glycolate, NF | 15.00 |
| Cysteine hydrochloride, USP | 18.00 |
| Talc, USP | 12.00 |
| Magnesium stearate, NF | 4.000 |
| CORE WEIGHT | 423.0 mg |
| (Coating) | |
| Opadry Red ®, YS-1-1846 | 12.00 |
| Carnauba Wax, NF | 0.0400 |
| TOTAL WEIGHT | 435.0 mg |

EXAMPLE 29

The procedure of example 24 was followed except:
Glycine hydrochloride is used as the stabilizer, giving the caplets the following composition:

| Ingredient | 100 mg potency caplet Weight (mg) per caplet |
|---|---|
| (Core) | |
| Bupropion hydrochloride | 100.00 |
| Microcrystalline cellulose, NF | 274.0 |
| Sodium starch glycolate, NF | 15.00 |
| Glycine hydrochloride, USP | 9.000 |
| Talc, USP | 12.00 |
| Magnesium stearate, NF | 4.000 |
| CORE WEIGHT | 414.0 mg |
| (Coating) | |
| Opadry Red ®, YS-1-1846 | 12.00 |
| Carnauba Wax, NF | 0.0400 |
| TOTAL WEIGHT | 426.0 mg |

EXAMPLE 30

The procedure of Example 24 was repeated except:
The blended powders were granulated with 100% Isopropyl alcohol.

We claim:

1. A pharmaceutical composition in solid form comprising bupropion hydrochloride and a pharmaceutically acceptable stabilizer in an effective stabilizing amount and which is solid or liquid at 30° C. wherein said stabilizer has a aqueous solution pH of about 0.9 to about 4 at an aqueous solution concentration of about 6% w/w, and said composition, when stored for 6 weeks at about 50 degrees C. and at about 27% relative humidity contains at least about 80% of the labelled amount of bupropion hydrochloride in the composition, said stabilizer selected from the group consisting of L-cysteine hydrochloride, glycine hydrochloride, malic acid, sodium metabisulfite, citric acid, tartaric acid and L-cystine dihydrochloride.

2. The composition of claim 1 in the form of a tablet or a capsule comprising bupropion hydrochloride and inactive ingredients wherein the weight of bupropion hydrochloride in the tablet or capsule is Y and the amount of inactive ingredients is greater than about 50% of Y and less than about 400% of Y.

3. The tablet of claim 2 in which the amount of bupropion hydrochloride in the tablet or capsule is 25 to 500 mg.

4. The tablet or capsule of claim 2 in which the amount of bupropion hydrochloride in the tablet is 50, 75, 100 or 150 mg.

5. The composition of claim 1 in the form of a tablet containing 25 to 300 mg of bupropion hydrochloride.

6. The composition of claims 1, 2, 3, 4, or 8 in which the amount of the stabilizer is 2.7% to 27% of the weight of bupropion hydrochloride in the composition.

7. The composition of claims 1, 2, 3, 4, or 8 in which the amount of stabilizer is 5% to 16.2% of the weight of bupropion hydrochloride in the composition.

8. A method of inhibiting degradation of bupropion hydrochloride in a tablet or capsule which comprises mixing bupropion hydrochloride with a stabilizer, having an aqueous solution pH between about 0.9 to 4 at an aqueous solution concentration of 6% w/w, in an amount of about 2.7% to about 27% of the weight of bupropion hydrochloride to form a solid form of the mixture in the form of a tablet or capsule, said tablet or capsule maintaining at least 80% of its initial potency after storage for six weeks at about 50° C. at about 27% humidity.

9. The method of claim 8 in which said amount of stabilizer is about 5% to about 16.2%.

10. The method of claim 7 or 8 in which the stabilizer is cysteine hydrochloride in the L form.

11. The method of claim 7 or 8 in which the stabilizer is glycine hydrochloride.

12. The composition of claim 1 in which the stabilizer is L-cystsine hydrochloride.

13. The composition of claim 2 in which the stabilizer is L-cystsine hydrochloride.

14. The composition of claim 3 in which the stabilizer is L-cystsine hydrochloride.

15. The composition of claim 4 in which the stabilizer is L-cystsine hydrochloride.

16. The composition of claim 14 in which the amount of stabilizer is 2.7% to 27% of the weight of bupropion hydrochloride in the composition.

17. The composition of claim 16 in which the amount of stabilizer is 5% to 16.2 of the weight of bupropion hydrochloride in the composition.

* * * * *